United States Patent
Beveridge et al.

(10) Patent No.: US 8,350,025 B2
(45) Date of Patent: Jan. 8, 2013

(54) PROCESS FOR PREPARING 6-PHENOXYPYRIMIDIN-4-OL DERIVATIVES IN THE PRESENCE OF A QUINUCLIDINE OR A N-METHYL PYRROLIDINE DERIVATIVES

(75) Inventors: Gillan Beveridge, Falkirk (GB); Ewan Campbell Boyd, Falkirk (GB); Jack Hugh Vass, Falkirk (GB); Alan John Whitton, Falkirk (GB)

(73) Assignee: Syngenta Limited, Surrey Research Park, Guildford, Surrey (GB)

( * ) Notice: Subject to any disclaimer, the term of this patent is extended or adjusted under 35 U.S.C. 154(b) by 360 days.

(21) Appl. No.: 12/444,866

(22) PCT Filed: Oct. 2, 2007

(86) PCT No.: PCT/GB2007/003733
§ 371 (c)(1),
(2), (4) Date: Nov. 4, 2009

(87) PCT Pub. No.: WO2008/043977
PCT Pub. Date: Apr. 17, 2008

(65) Prior Publication Data
US 2010/0063275 A1    Mar. 11, 2010

(30) Foreign Application Priority Data
Oct. 9, 2006  (GB) .................................. 0619942.6

(51) Int. Cl.
*C07D 413/12* (2006.01)
(52) U.S. Cl. ................. 544/2; 544/65; 544/66; 544/319
(58) Field of Classification Search ................ 544/2, 65, 544/66, 319
See application file for complete search history.

(56) References Cited

FOREIGN PATENT DOCUMENTS
| | | |
|---|---|---|
| DE | 4340181 | 6/1995 |
| WO | 9417060 | 8/1994 |
| WO | 0172719 | 10/2001 |

*Primary Examiner* — Brian McDowell
(74) *Attorney, Agent, or Firm* — Kody Jones

(57) ABSTRACT

The present invention relates, inter alia, to a process for preparing a compound of formula (I): using a quinuclidine-based catalyst or an optionally 3-substituted N-methyl pyrrolidine-based catalyst.

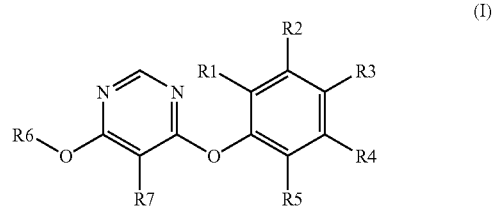

(I)

31 Claims, No Drawings

PROCESS FOR PREPARING 6-PHENOXYPYRIMIDIN-4-OL DERIVATIVES IN THE PRESENCE OF A QUINUCLIDINE OR A N-METHYL PYRROLIDINE DERIVATIVES

This application is a 371 of International Application No. PCT/GB2007/003733 filed Oct. 2, 2007, which claims priority to GB 0619942.6 filed Oct. 9, 2006, the contents of which are incorporated herein by reference.

The present invention relates to a process for preparing asymmetrical 4,6-bis(aryloxy)pyrimidines derivatives. In particular, the present invention provides a process for preparing strobilurin fungicides such as methyl (E)-2-{2-[6-(2-cyanophenoxy)pyrimidin-4-yloxy]phenyl}-3-methoxyacrylate (azoxystrobin).

Methods for preparing azoxystrobin are described in WO 92/08703. In one method, azoxystrobin is prepared by reacting 2-cyanophenol with methyl (E)-2-[2-(6-chloropyrimidin-4-yloxy)phenyl]-3-methoxyacrylate. A high-yielding method for producing asymmetrical 4,6-bis(aryloxy)pyrimidine derivatives is disclosed in WO 01/72719 in which a 6-chloro-4-aryloxypyrimidine is reacted with a phenol, optionally in the presence of a solvent and/or a base, with the addition of from 2 to 40 mol % of 1,4-diazabicyclo[2.2.2] octane (DABCO).

Surprisingly, it has now been found that certain quinuclidine-based catalysts and pyrrolidine-based catalysts are also able to catalyse this reaction.

Thus, according to the present invention, there is provided a method for preparing a compound of formula (I)

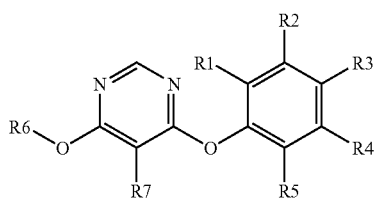

(I)

which comprises either:
a) reacting a compound of formula (II)

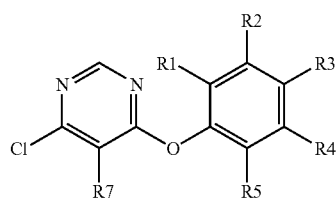

(II)

with a compound of formula R6-OH, or a salt thereof, in the presence of between 0.05 and 40 mol % of
(i) a quinuclidine-based molecule of formula (VI):

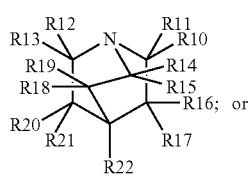

(VI)

(ii) the acid salt of the quinuclidine-based molecule of formula (VI); or
(iii) an optionally 3-substituted N-methyl pyrrolidine of formula (VII):

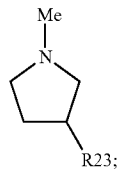

(VII)

(iv) the acid salt of the optionally 3-substituted N-methyl pyrrolidine of formula (VII);
or
b) reacting a compound of formula (III)

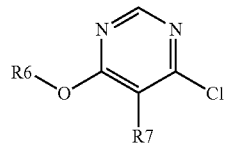

(III)

with a compound of formula (IV)

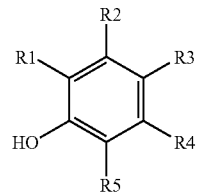

(IV)

or a salt thereof, in the presence of between 0.05 and 40 mol % of
(i) a quinuclidine-based molecule of formula (VI):

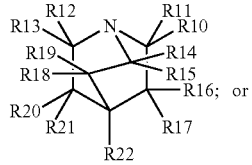

(VI)

(ii) the acid salt of the quinuclidine-based molecule of formula (VI); or
(iii) an optionally 3-substituted N-methyl pyrrolidine of formula (VII):

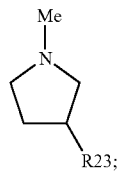

(VII)

(iv) the acid salt of the optionally 3-substituted N-methyl pyrrolidine of formula (VII);
wherein:
(i) R1, R2, R3 and R4 are, independently, hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulphonyl;
(ii) R5 is hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulponyl, or

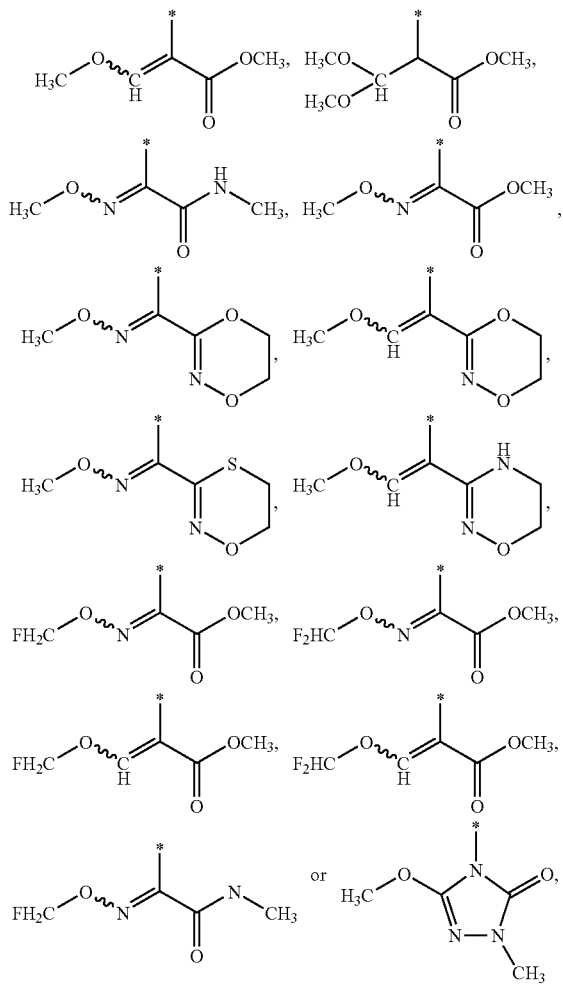

wherein * denotes the point of attachment to the phenyl radical of formula (I);
(iii) R6 is substituted or unsubstituted aryl or heterocyclyl, or a salt thereof;
(iv) R7 is hydrogen, fluorine, chlorine or bromine,
(v) R10, R11, R12, R13, R14 and R15 are, independently, hydrogen, fluorine, methyl, methoxy, methylene or cyano, or, independently, R10 and R11, R12 and R13, R14 and R15 together form =O, =S, =N or =CR30R31, wherein R30 and R31 are, independently, hydrogen or a substituent;
(vi) R16, R17, R18, R19, R20 and R21 are, independently, hydrogen, fluorine, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy, optionally substituted silyloxy, or, independently, R16 and R17, R18 and R19 and R20 and R21 together form =O, =S, =N or =CR30R31, wherein R30 and R31 are, independently, hydrogen or a substituent;
(vii) R22 is hydrogen, fluorine, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy or optionally substituted silyloxy;
(viii) R23 is hydrogen or a $C_{1-4}$ straight chain or branched alkyl,
with the proviso that R6 and the radical:

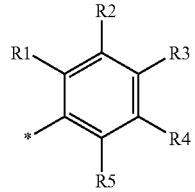

are different from each other.
In a particular embodiment of the invention, the catalyst is a quinuclidine based molecule of formula (VI) or a salt of the molecule of formula (VI). In a further embodiment, the catalyst is quinuclidine, quinuclidinol or quinuclidinone or a quinuclidine-based molecule of formula (VI) in which R10 to R15 and R18 to 22 are hydrogen and (i) R16 is hydrogen and R17 is fluorine, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy or optionally substituted silyloxy, or (ii) R17 is hydrogen and R16 is fluorine, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy or optionally substituted silyloxy.

In a yet further embodiment of the invention, the catalyst is quinuclidine, 3-quinuclidinol or 3-quinuclidinone or an acid salt of quinuclidine, 3-quinuclidinol or 3-quinuclidinone. In a further embodiment of the invention, the catalyst is quinuclidine or 3-quinuclidinol or an acid salt thereof. Suitably, the acid salt is the hydrochloride salt.

In a particular embodiment of the invention, the catalyst is an optionally 3-substituted N-methyl pyrrolidine of formula (VII) or an acid salt thereof. In a further embodiment, the compound of formula (VII) is N-methyl pyrrolidine or an acid salt thereof.

In a particular embodiment of the invention, the catalyst may be bound to a polymeric support through one of the substituent groups R16 to R22. Suitable polymeric supports include, but are not limited to functionalised cross-linked polystyrenes and silica gels or silica gels via suitable linking radicals.

The starting materials R6-OH and formulae (II), (III), (IV) and the end product of formula (I) can be present as pure isomers of different possible isomeric forms, for example E or Z isomers or, as appropriate, as mixtures of different possible isomeric forms, in particular of heteroisomers, such as for example, E/Z mixtures.

Suitably, R1, R2, R3 and R4 are, independently, hydrogen, halogen, cyano, nitro, formyl, alkylcarbonyl, alkoxycarbonyl, aminocarbonyl, alkylaminocarbonyl, dialkylaminocarbonyl or alkyl, alkoxy, alkylthio, alkylsulphinyl or alkylsulphonyl optionally substituted with 1 to 5 halogen atoms.

More suitably, R1, R2, R3 and R4 are, independently, hydrogen, fluorine, chlorine, bromine, cyano, nitro, acetyl, propionyl, methoxycarbonyl, ethoxycarbonyl, aminocarbonyl, methylaminocarbonyl, ethylaminocarbonyl, dimethylaminocarbonyl, diethylaminocarbonyl, methyl, ethyl, n- or i-propyl, n-, s- or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

Even more suitably, R1, R2, R3 and R4 are, independently, hydrogen or methyl.

Most suitably, R1, R2, R3 and R4 are each hydrogen.

Suitably, R5 is hydrogen, halogen, cyano, nitro, formyl, alkylcarbonyl, alkoxycarbonyl, aminocarbonyl, alkylaminocarbonyl, dialkylaminocarbonyl or alkyl, alkoxy, alkylthio, alkylsulphinyl or alkylsulphonyl optionally substituted with 1 to 5 halogen atoms or

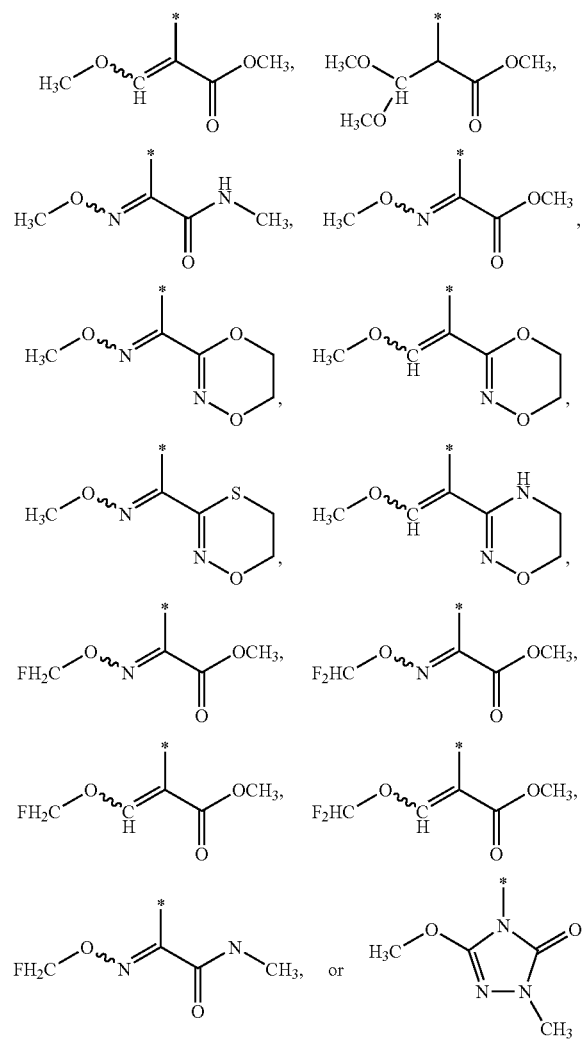

wherein * denotes the point of attachment to the phenyl radical. In addition, the process of the present invention may also be carried out using compounds of formula (II) or (IV) in which R5 is a mixture of the groups listed above.

More suitably, R5 is:

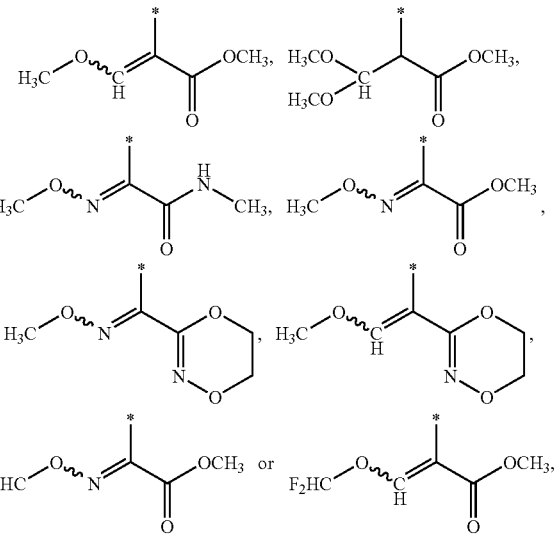

or a mixture thereof, where * denotes the point of attachment to the phenyl radical.

Most suitably, R5 is:

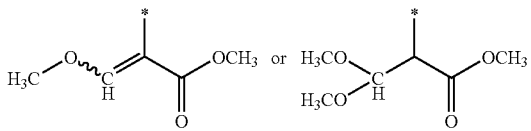

or a mixture thereof, where * denotes the point of attachment to the phenyl radical.

Suitably, R6 is:
(a) a heterocycle having 3 to 7 ring members, optionally substituted by halogen or by $C_{1-6}$ alkyl, $C_{1-6}$ alkoxy, $C_{1-6}$ halogenoalkyl or $C_{1-6}$ halogenoalkoxy; or
(b) phenyl or naphthyl, each of which is optionally mono- to pentasubstituted by identical or different substituents selected from the group comprising:
  (i) halogen, cyano, formyl or acetal protected formyl (for example the dimethyl or diethyl acetal, 1,3-dioxolan-2-yl, 1,3-dioxan-2-yl) carboxyl, carbamoyl, thiocarbamoyl, aminocarbonyl;
  (ii) $C_{1-8}$, straight-chain or branched, alkyl, oxyalkyl, alkoxy, alkoxyalkyl, alkylthioalkyl, dialkoxyalkyl, alkylthio, alkylsuphinyl or alkylsulphonyl having in each case 1 to 8 carbon atoms;
  (iii) $C_{2-6}$, straight-chain or branched, alkenyl or alkenyloxy;
  (iv) $C_{1-6}$, straight-chain or branched, halogenoalkyl, halogenoalkoxy, halogenoalkylthio, halogenoalkylsulphinyl or halogenoalkylsulphonyl with between 1 and 13 identical or different halogen atoms;
  (v) $C_{2-6}$, straight chain or branched, halogenoalkenyl or halogenoalkenyloxy with between 1 and 11 identical or different halogen atoms;
  (vi) $C_{1-6}$, straight-chain or branched, dialkylamino; alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkynylcarbonyl;

(vii) $C_{3-6}$ cycloalkyl or cycloalkyloxy;
(viii) doubly attached $C_{3-4}$ alkylene, $C_{2-3}$ oxyalkylene or $C_{1-2}$ dioxyalkylene, each of which is optionally mono- to tetrasubstituted by identical or different substituents selected from the group consisting of fluorine, chlorine, oxo, methyl, trifluoromethyl and ethyl; or
(ix) the group

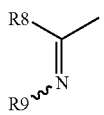

in which:
R8 is hydrogen, hydroxyl, $C_{1-4}$ alkyl or $C_{1-6}$ cycloalkyl; and
R9 is
 i. hydroxyl, methoxy, ethoxy, amino, methylamino, phenyl or benzyl; or
 ii. $C_{1-4}$ alkyl or alkoxy, optionally substituted with cyano-, alkoxy-, alkylthio-, alkylamino-, dialkylamino- or phenyl;
 iii. $C_{2-4}$ alkenyloxy or alkynyloxy;
 iv. benzoyl, benzoylethenyl, cinnamoyl, heterocyclyl; or
 v. phenylalkyl, phenylalkyloxy or heterocyclylalkyl, having in each case 1 to 3 carbon atoms in the alkyl moieties and being in each case optionally mono- to trisubstituted in the ring moiety by halogen and/or straight-chain or branched $C_{1-4}$ alkyl or alkoxy.

More suitably, R6 is:
(a) thienyl, pyridyl or furyl optionally substituted with methyl, ethyl, methoxy, ethoxy, trifluoromethyl or trifluoromethyoxy; or
(b) phenyl, optionally mono- to pentasubstituted by identical or different substituents selected from:
 (i) fluorine, chlorine, bromine, iodine, cyano, nitro, formyl or acetal protected formyl (for example the dimethyl or diethyl acetal, 1,3-dioxolan-2-yl, 1,3-dioxan-2-yl), carboxy, carbamoyl, thiocarbamoyl, methyl, ethyl, n- or i-propyl, n-, i-, s-, or t-butyl, 1-, 2-, 3- or neo-pentyl, 1-, 2,-3, or 4-(2-methylbutyl), 1-, 2- or 3-hexyl, 1-, 2-, 3-, 4- or 5-(2-methylpentyl), 1-, 2- or 3-(3-methylpentyl), 2-ethylbutyl, 1-, 3- or 4-(2,2-dimethylbutyl), 1- or 2-(2, 3-dimethylbutyl), 3-oxobutyl, methoxymethyl, dimethoxymethyl, methoxy, ethoxy, n- or i-propoxy, methylthio, ethylthio, n- or i-propylthio, methylsulpinyl, ethylsulphinyl, methylsulphonyl or ethylsulphonyl, vinyl, allyl, 2-methylallyl, propene-1-yl, crotonyl, propargyl, vinyloxy, allyloxy, 2-methylallyoxy, propene-1-yloxy, crotonyloxy, propargyloxy, trifluoromethyl, trifluoroethyl, difluoromethoxy, trifluoromethoxy, difluorochloromethoxy, trifluoromethoxy, difluoromethylthio, trifluoromethylthio, difluorochloromethylthio, trifluoromethylsulphinyl, trifluoromethylsulphonyl, dimethylamino, diethylamino, acetyl, propionyl, $C_{1-6}$ alkoxycarbonyl, aminocarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl;
 (ii) in each case double attached propanediyl or ethyleneoxy, each of which is optionally mono- to tetrasubstituted by identical or different substituents selected from the group consisting of fluorine, chlorine, oxo, methyl and trifluoromethyl, or
 (iii) the group:

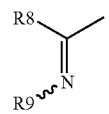

where R8 is hydrogen, methyl or hydroxyl and R9 is
 i. hydroxyl, methoxy, ethoxy, amino, methylamino, phenyl or benzyl,
 ii. phenyl, benzoyl, benzoylethenyl, cinnamoyl, benzyl, phenylethyl, phenylpropyl, benzyloxy, 5,6-dihydro-1,4,4-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms.

More suitably, R6 is optionally mono- to pentasubstituted phenyl where the substituents are selected from halogen, cyano, formyl or acetal protected formyl (for example the dimethyl or diethyl acetal, 1,3-dioxolan-2-yl, 1,3-dioxan-2-yl), methoxycarbonyl, ethoxycarbonyl, aminocarbonyl, methylaminocarbonyl, ethylaminocarbonyl, dimethylaminocarbonyl, diethylaminocarbonyl, in each case straight-chain or branched $C_{1-4}$ alkyl or halogenoalkyl or the group:

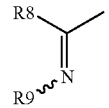

wherein R8 is hydrogen and R9 is hydroxyl, methoxy or ethoxy.

Even more suitably, R6 is optionally mono- to pentasubstituted phenyl where the substituents are selected from halogen, cyano, in each case straight-chain or branched alkyl or halogenoalkyl having in particular 1 to 4 carbon atoms.

Most suitably, R6 is cyanophenyl and, in particular, the R6-OH group is 2-cyanophenol.

Suitably, R7 is hydrogen, fluorine or chlorine, and most suitably, R7 is hydrogen.

In a preferred embodiment, R1, R2, R3 and R4 are hydrogen, R5 is

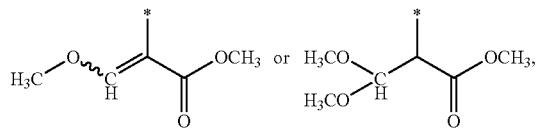

or a mixture thereof, R6 is 2-cyanophenyl and R7 is hydrogen.

In the definitions above, and unless specified otherwise:
(a) Saturated or unsaturated hydrocarbon chains, such as alkyl, alkanediyl, alkenyl or alkynyl, may be straight-chain or branched. Suitably, and unless specified otherwise, alkyl and alkyl-derived chains have 1 to 6 carbon atoms and alkenyl and alkenyl-derived chains as well as alkynyl and alkynyl-derived chains have 2 to 6 carbon atoms. Hydrocarbon chains may include heteroatoms (for example, they may be alkoxy, alkylthio or alkylamino groups) and may also be mono- or polysubstituted by e.g. halogen atoms and/or hydroxyl groups (for example halogenoalkyl, halogenoalkoxy, hydroxyalkyl).

(b) Halogen or halogen means fluorine, chlorine, bromine or iodine. Suitably, halogen or halogeno means fluorine, chlorine or bromine. Most suitably, halogen or halogen means fluorine or chlorine.

(c) Aryl groups are aromatic, mono or polycyclic hydrocarbon rings, such as, for example, phenyl, naphthyl, anthranyl, phenanthryl. Suitably aryl groups are phenyl or naphthyl and most suitably are phenyl.

(d) Heterocyclyl groups are saturated or unsaturated (and may be aromatic), cyclic compounds where at least one ring member is a heteroatom, i.e. an atom different from carbon. If the ring contains a plurality of heteroatoms, they may be identical or different. Suitable heteroatoms are oxygen, nitrogen or sulphur. The cyclic components may form a polycyclic ring system together with other carbocyclic or heterocyclic, fused-on or bridged rings. Suitably, heterocyclyl groups may be mono- or bicyclic ring systems, and more suitably, mono- or bicyclic aromatic ring systems. Heterocyclyl groups may also be mono- or polysubstituted, suitably by methyl, ethyl or halogen.

(e) Cycloalkyl groups are saturated carbocyclic compounds, which may form polycyclic ring systems together with other carbocyclic fused-on or bridged rings. Polycyclic ring systems may also be attached to heterocyclic groups or ring systems.

The above mentioned general or preferred radical definitions apply both to the end product of formula (I) and to the starting materials required for the preparation of formula (I).

In a further preferred embodiment, the process of invention comprises reacting a compound of formula (V):

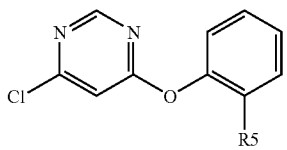

wherein R5 is

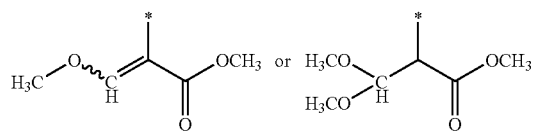

or a mixture thereof with 2-cyanophenol, or a salt thereof (suitably sodium or potassium 2-cyanophenoxide) in the presence of between 0.05 and 40 mol % of a catalyst as defined above.

When the process of the invention is carried out as described in the embodiment detailed immediately above, or using a compound of formula (IV), where R5 is

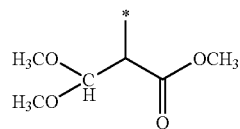

(methyl 2-(3,3-dimethoxy)propanoate), the product obtained may include a proportion of the compound of formula (I) where R5 is

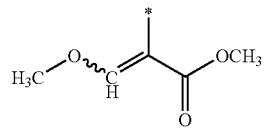 [SMILES: *C(=COC)C(=O)OC]

(methyl (E)-2-(3-methoxy)acrylate).

This may happen because it is possible that methanol is eliminated from the methyl 2-(3,3-dimethoxy)propanoate group under the conditions of the process. For the same reason, if the process is carried out using a compound of formula (II) or a compound of formula (IV) where R5 is a mixture of the methyl 2-(3,3-dimethoxy)propanoate group and the methyl (E)-2-(3-methoxy)acrylate group, the product obtained will be a compound of formula (I) where R5 is a mixture of the methyl 2-(3,3-dimethoxy)propanoate group and the methyl (E)-2-(3-methoxy)acrylate group; however, the product may have a higher proportion of the compound of formula (I) where R5 is the methyl (E)-2-(3-methoxy)acrylate group than expected from the proportion of methyl (E)-2-(3-methoxy)acrylate group in the mixed starting material due to this potential elimination of methanol. This is of no real consequence because it will normally be required to convert the product of formula (I) where R5 is the methyl 2-(3,3-dimethoxy)propanoate group to the compound of formula (I) where R5 is the group methyl (E)-2-(3-methoxy)acrylate group by the elimination of methanol.

Conveniently the process of the invention is carried out in a suitable inert solvent or diluent. These include, for example, aliphatic, alicyclic and aromatic hydrocarbons, such as petroleum ether, hexane, heptane, cyclohexane, methylcyclohexane, benzene, toluene, xylene and decalin; halogenated hydrocarbons, such as chlorobenzene, dichlorobenzene, dichloromethane, chloroform, carbon tetrachloride, dichloroethane and trichloroethane; heteroaromatic solvents such as pyridine or a substituted pyridine, for example, 2,6-dimethylpyridine; ethers, such as diethyl ether, diisopropylether, methyl-tert-butyl ether, methyl-tent-amyl ether, dioxane, tetrahydrofuran, 1,2-dimethoxyethane, 1,2-diethoxyethane and anisole; ketones, such as acetone, butanone, methyl isobutyl ketone and cyclohexanone; nitriles, such as acetonitrile, propionitrile, n- and i-butyronitrile and benzonitrile; amides, such as N,N-dimethylformamide, N,N-dimethylacetamide, N-methylformamide, N-methyl-pyrrolidone and hexamethylphosphoric triamide; tertiary amines, in particular, amines of the formula R'R"R'"N where R', R" and R'" are each independently $C_{1-10}$ (especially $C_{1-8}$) alkyl, $C_{3-6}$ cycloalkyl, aryl (especially phenyl) or aryl($C_{1-4}$)alkyl (especially benzyl); or two or three of R', R" and R'" join together with the nitrogen atom to which they are attached to faun one, two or three 5-, 6- or 7-membered alicyclic rings optionally fused and optionally containing a second ring nitrogen atom, examples of suitable tertiary amines being N,N-diisopropylethylamine (Hünig's base), N,N-dimethylaniline, triethylamine, t-butyldimethylamine, N,N-diisopropylmethylamine, N,N-diisopropylisobutylamine, N,N-diisopropyl-2-ethylbutylamine, tri-n-butylamine, N,N-dicyclohexylmethylamine, N,N-dicyclohexylethylamine, N-tert-butylcyclohexylamine, N,N-dimethylcyclohexylamine, 1,5-diazabicyclo[4.3.0]-non-5-ene, 1,8-diazabicyclo[5.4.0]undec-7-ene or 2-dimethylaminopyridine; esters, such as methyl acetate, ethyl acetate and isopropyl acetate; sulphoxides, such as dimethylsulphoxide; sulphones, such as dimethylsulphone and sulpholane; and mixtures of such solvents and diluents and mixtures of one or more of them with water. In addition, if the starting compounds for the reaction or product from the reaction are in the form of liquids or will be liquid at the reaction temperature, they may act as a diluent/solvent for the process of the invention. In such a situation, an additional solvent or diluent is not required.

Particularly suitable diluents are ketones [such as methyl isobutyl ketone and cyclohexanone], esters [such as isopropyl acetate], tertiary amines [such as [N,N-diisopropylethylamine (Hünig's base)] and amides [such as N,N-dimethylformamide]. In a particular aspect of the present invention, methyl isobutyl ketone is used as diluent. In a further aspect of the present invention, cyclohexanone is used as diluent. In a further aspect of the present invention, isopropyl acetate is used as diluent. In a further aspect of the present invention, N,N-dimethylformamide is used as diluent. In a further aspect of the present invention, N,N-diisopropylethylamine (Hünig's base) is used as diluent. Most suitably, the diluent used in the present invention is N,N-dimethylformamide.

In a further embodiment of the present invention, the process is carried out in aqueous organic solvent system. Suitably, in this embodiment, when the compound of formula (II) is reacted with R6-OH or the compound of formula (III) is reacted with the compound of formula (IV), the R6-OH or the compound of formula (IV) is present as a salt. This salt may either have been added as is or generated in situ from the neutral phenol and the acid acceptor (see below). Suitably, the salt is a lithium, caesium, sodium, potassium, 1,5-diazabicyclo[4.3.0]non-5-ene or 1,8-diazabicyclo[5.4.0]undec-7-ene salt of R6-OH or the compound of formula (IV). More suitably, the salt is the 1,8-diazabicyclo[5.4.0]undec-7-ene, sodium or potassium salt. For example, when R6-OH is 2-cyanophenol, the 2-cyanophenol is present as a salt, suitably sodium or potassium 2-cyanophenoxide. Suitable co-solvents for use in such an aqueous process are solvents which are at least partially water immiscible solvents such as cyclohexanone, methyl isobutyl ketone and isopropyl acetate. Advantageously, the water is removed throughout the reaction when these partially water immiscible solvents are used. In addition, it has also been found that water, miscible solvents may also be used in such an aqueous process. Suitable water miscible solvents are N,N-dimethylformamide, N,N-dimethylacetamide, N-methylpyrrolidinone and dimethyl sulphoxide. In one embodiment, the water is removed throughout the reaction when the water miscible solvents are used. Most suitably, when such aqueous systems are used, and R6-OH is 2-cyanophenol, the salt used is potassium 2-cyanophenoxide and the diluent is cyclohexanone, methyl isobutyl ketone, isopropyl acetate, or N,N-dimethylformamide. It is noted that when the R6-OH or the compound of formula (IV) is added to the process as an aqueous salt solution it is possible to reduce the quantity of acid acceptor (see below) used.

In addition, the process of the invention is preferably carried out in the presence of an acid acceptor. Suitable acid acceptors are all customary inorganic and organic bases. These include, for example, alkaline earth metal and alkali metal hydroxides, acetates, carbonates, bicarbonates phosphates, hydrogen phosphates and hydrides [such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride], guanidines, phosphazines (see, for example, Liebigs Ann. 1996, 1055-1081), prophosphatranes (see, for example, JACS 1990, 9421-9422), metal dialkylamides [such as lithium di-iso-propylamide] and tertiary amines [such as those described above as possible solvents or diluents]. Particularly suitable acid acceptors are the alkaline earth metal and alkali metal carbonates, especially potassium carbonate and sodium carbonate and the tertiary amines 1,5-diazabicyclo[4.3.0]non-5-ene and 1,8-diazabicyclo[5.4.0]undec-7-ene. More suitably, the acid acceptor is potassium carbonate. Most suitably, the present invention is carried out in the presence of methyl isobutyl ketone, cyclohexanone, isopropyl acetate, N,N-diisopropylethylamine (Hünig's base) or N,N-dimethylformamide with potassium carbonate as the acid acceptor.

In order to enhance the rate of reaction, it may be advantageous to increase the solubility of the acid acceptor and R6-OH anion, or the anion of the compound of formula (IV), in the selected reaction solvent, in ways known to the skilled person, for example, by addition of compounds which might include phase transfer agents such as quaternary ammonium salts ($R_4N^+$), quaternary phosphonium salts ($R_4P^+$), crown ether or polyethers such as polyethylene glycol (HO[$CH_2CH_2O$]$_n$H), polypropylene glycol (HO[$CH_2CH_2CH_2O$]$_n$H or the methyl or ethyl ethers of such (R'O[$CH_2CH_2O$]$_n$R", R'O[$CH_2CH_2CH_2O$]$_n$R") wherein the R radicals can be the same or different and include straight or branched chain $C_{1-12}$ alkyl, optionally substituted aryl or benzyl and R' and R" can be the same or different and can be any straight chain or branched $C_{1-4}$ alkyl and n=1-20.

Suitably, the process of the invention is carried out in the presence of between 0.05 and 40 mol % of catalyst, the catalyst being selected from (i) a quinuclidine-based molecule of formula (VI) as defined above; (ii) the acid salt of the quinuclidine-based molecule of formula (VI); (iii) a 3-substituted N-methyl pyrrolidine of formula (VII) as defined above or (iv) the acid salt of the optionally 3-substituted N-methyl pyrrolidine of formula (VII). Any amount of catalyst between 0.1 and 20 mol % of catalyst, or between 0.1 and 10 mol % of catalyst, or between 0.1 and 5 mol % of catalyst is suitable for use in the present invention but, most suitably, between 0.2 and 5 mol % of catalyst is used.

In a particular embodiment of the invention the process is carried out in the presence of about 0.2 mol % to about 5 mol % quinuclidine hydrochloride or 3-quinuclidinol hydrochloride with methyl isobutyl ketone, cyclohexanone, isopropyl acetate, N,N-diisopropylethylamine (Hünig's base), or N,N-dimethylformamide as diluent. More suitably, the diluent is N,N-dimethylformamide or isopropyl acetate. Most suitably the diluent is N,N-dimethylformamide. Suitably, the acid acceptor will be potassium carbonate.

When carrying out the process of the invention, the reaction temperature can be varied within a relatively wide range. The temperature chosen will depend on the nature of the solvent or diluent, for example on its boiling point and/or its effectiveness for promoting the desired reaction, and on the rate at which the reaction is to be carried out. In any given solvent or diluent, the reaction will tend to progress more slowly at lower temperatures. In general, the reaction may be carried out at a temperature of from 0 to 120° C., suitably at a temperature of from 40 to 100° C., and typically at a temperature of from 45 to 95° C., for example, from 60 to 85° C.

The process of the invention can be carried out at any reasonable pressure depending on the solvent, base and reaction temperature. For low boiling diluents or reagents, higher temperatures can be accessed by reaction at higher than atmospheric pressures, and reactions can be carried out at atmospheric pressures or under vacuum if desired. In general, the reaction may be carried out at a pressure of from 0.01 to 10 Bara, suitably at the pressure of from 0.5-5 Bara, typically at a pressure of from 0.8 to 2 Bara, for example at ambient pressure.

For carrying out the process of the invention, from 0.8 to 4 mol, usually from 0.95 to 1.2 mol, of R6-OH is employed per mol of a compound of formula (II); and similar amounts (0.8 to 4 mol, usually from 0.95 to 1.2 mol) of a compound of formula (IV) are employed per mole of the compound of formula (III).

Conveniently the process of the invention is carried out by mixing one of the components of the reaction, preferably in the presence of a solvent or diluent, with an acid acceptor. The other component is then added, if appropriate in the presence of a solvent or diluent, and the mixture is stirred, normally at an elevated temperature. The catalyst may be added at any stage to start the reaction and after the reaction is judged to be complete, the reaction mixture is worked up and the product is isolated using conventional techniques well known to a skilled chemist. As stated above, the catalyst may be added at any stage but it is preferable that catalyst is not mixed with the compound of formula (II) or the compound of formula (III) in the absence of R6-OH or the compound of formula (IV), respectively. Following this order of addition tends to promote higher product yields and a faster reaction rate. While not wanting to be bound by theory, it is believed that, in the absence of R6-OH or the compound of formula (IV), the catalyst and the compounds of formula (II) or (III) react and then the reaction product can further convert to give a non-active species, thus reducing yield and available catalyst. In the presence of R6-OH or the compound of formula (IV), the reaction product of the catalyst and the compounds of formula (II) or (III) reacts with the salt of 2-cyanophenol or a phenate salt of a compound of formula (IV) to give the expected product of formula (I) and, concomitantly, regenerates the catalyst.

Of course, if the catalyst is not able to react with the compound of formula (II) or the compound of formula (III), then they can be mixed with impunity. However, in such a case, before the conditions are made suitable for the reaction to take place, 2-cyanophenol or the compound of formula (IV) must be added. This may occur, for example, if both components are in a solid state or perhaps if the catalyst is not very soluble in the solvent carrying the compound of formula (II) or the compound of formula (III). In such a situation, any reaction between the catalyst and the compounds of formula (II) or (III) before R6-OH or the compound of formula (IV) are added will be insignificant and will not affect the overall reaction rate/yield.

Thus, it is preferable that the catalyst is not mixed with the compound of formula (II) or the compound of formula (III) unless (i) R6-OH or the compound of formula (IV) is present; or (ii) conditions are such that the catalyst and the compound of formula (II) or the compound of formula (III) are not able to react with each other.

The compounds of R6-OH required as starting materials for carrying out the process according to the invention are commercially available or can be made from commercially available starting materials using literature processes.

The compounds of formula (II) and (III) may be prepared, for example, as discussed in U.S. Pat. No. 6,734,304 (the contents of which are herein incorporated by reference). In particular, the compound of formula (II), where R5 is the methyl (E)-2-(3-methoxy)acrylate group $C(CO_2CH_3)$=$CHOCH_3$, and the compound of formula (II) where R5 is the methyl 2-(3,3-dimethoxy)propanoate group $C(CO_2CH_3)CH(OCH_3)_2$, may be prepared as described in WO 92/08703 from the reaction of 3-(α-methoxy)methylenebenzofuran-2(3H)-one (derived from benzofuran-2(3H)-one) with 4,6-dichloropyrimidine. The compound of formula (II), where R5 is the methyl (E)-2-(3-methoxy)acrylate group, may also be prepared by eliminating methanol from (that is, by the demethanolysis of) the compound of formula (II) where R5 is the methyl 2-(3,3-dimethoxy)propanoate group, as described in WO 92/08703 or WO 98/07707. The compound of formula (II), where R5 is the methyl 2-(3,3-dimethoxy)propanoate group, may be prepared as described in GB-A-2291874 by reacting a compound of formula (IV), where R5 is the methyl 2-(3,3-dimethoxy)propanoate group, with 4,6-dichloropyrimidine. It may be purified before use by known techniques or may be used in an unpurified state from a previous reaction, for example, in a 'one-pot' reaction.

The compounds of formula (IV) are also known and may be prepared by known methods, references to which are given in U.S. Pat. No. 6,734,304. In particular, the compound of formula (IV), where R5 is the methyl 2-(3,3-dimethoxy)propanoate group, may be prepared as described in GB-A-2291874 from 3-(α-methoxy)methylenebenzofuran-2(3H)-one. The compound of formula (IV), where R5 is the methyl (E)-2-(3-methoxy)acrylate group, may be prepared by the procedure described in EP 0 242 081 or by the demethanolysis of the compound of formula (IV) where R5 is the methyl 2-(3,3-dimethoxy)propanoate group. In this case the phenolic group needs to be protected by, for example, benzylation before demethanolysis and then de-protected.

The following Examples illustrate the invention. The examples are not intended as necessarily representative of the overall testing performed and are not intended to limit the invention in any way.

EXAMPLES

In these examples:
DABCO=diazabicyclclo[2.2.2]octane
DMAP=4-dimethylaminopyridine
MIBK=methylisobutylketone
DMF=dimethylformamide Example 1

Screening Experiments to Identify Potential Catalysts

Methyl (E)-2-{2-[6-chloropyrimidin-4-yloxy]phenyl}-3-methoxyacrylate (II) (3 g of 95.4% strength) was charged to the reaction tube followed by the solvent (10 ml) then 2-cyanophenol (1.2 g), base (1.5 mol equivalents) and the compound being tested as a catalyst (15 mol %). The reaction mixtures were held, with stirring, at 40° C. for 4 hrs, then at 60° C. for 2 hrs. The reaction was monitored for formation of product, throughout the hold period, by Gas Chromatography. Results are recorded as area % levels of methyl (E)-2-{2-[6-chloropyrimidin-4-yloxy]phenyl}-3-methoxyacrylate (II) and methyl (E)-2-{2-[6-(2-cyanophenoxy)pyrimidin-4-yloxy]phenyl}-3-methoxyacrylate (I) in the reaction mixture.

The following systems were tested:

TABLE 1

| No. | Solvent | Catalyst | Base |
|---|---|---|---|
| 1.1 | DMF | No Catalyst | $K_2CO_3$ (1.9 g) |
| 1.2 | Toluene | DABCO (0.15 g) | $K_2CO_3$ (1.9 g) |
| 1.3 | Toluene | DABCO (0.15 g) | $Na_2CO_3$ (1.4 g) |
| 1.4 | DMF | Triethylamine (0.14 g) | $K_2CO_3$ (1.9 g) |
| 1.5 | DMF | Tetramethylenediamine (0.16 g) | $K_2CO_3$ (1.9 g) |
| 1.6 | DMF | 1-Methylpyrrolidine (0.11 g) | $K_2CO_3$ (1.9 g) |
| 1.7 | DMF | Dimethyloctylamine (0.21 g) | $K_2CO_3$ (1.9 g) |
| 1.8 | DMF | Dimethylaminopolystyrene (0.45 g) | $K_2CO_3$ (1.9 g) |
| 1.9 | DMF | DABCO (0.15 g) | $K_2CO_3$ (1.9 g) |
| 1.10 | Cyclohexanone | DABCO (0.15 g) | $K_2CO_3$ (1.9 g) |
| 1.11 | MIBK | DABCO (0.15 g) | $K_2CO_3$ (1.9 g) |
| 1.12 | Cyclohexanone | 1-Methylpyrrolidine (0.11 g) | $K_2CO_3$ (1.9 g) |
| 1.13 | DMF | Quinuclidine Hydrochloride (0.21 g) | $K_2CO_3$ (1.9 g) |
| 1.14 | Cyclohexanone | Tetramethylenediamine (0.16 g) | $K_2CO_3$ (1.9 g) |

The results are shown in Table 2 below:

TABLE 2

| No. | 4 hr at 40° C. | | +2 hr at 60° C. | |
|---|---|---|---|---|
| | Residual (II) | (I) Formed | Residual (II) | (I) Formed |
| 1.1 | 89.0% | 10.7% | 64.9% | 34.8% |
| 1.2 | 9.8% | 89.8% | 0.3% | 99.1% |
| 1.3 | 74.2% | 25.5% | 22.7% | 76.9% |
| 1.4 | 93.6% | 5.9% | 70.2% | 28.9% |
| 1.5 | 78.4% | 21.3% | 48.8% | 50.0% |
| 1.6 | 31.1% | 68.5% | 10% | 88.2% |
| 1.7 | 69.5% | 30.2% | 51% | 47.8% |
| 1.8 | 89.7% | 9.9% | 63.2% | 35.7% |
| 1.9 | 0.2% | 98.1% | 0.2% | 97.9% |
| 1.10 | 0.5% | 99.0% | 0.2% | 98.2% |
| 1.11 | 2.0% | 96.5% | 0.2% | 99.4% |
| 1.12 | 49.8% | 49.4% | 22.7% | 76.0% |
| 1.13 | 0.2% | 99.6% | 0.2% | 98.2% |
| 1.14 | 93.2% | 6.5% | 82% | 17.6% |

Further screening experiments, using DMF as a solvent, were carried out as detailed below:

Methyl (E)-2-{2-[6-chloropyrimidin-4-yloxy]phenyl}-3-methoxyacrylate (II) (6.4 g of 45.2% strength solution in DMF) was charged to the reaction tube followed by further DMF (6.4 g), 2-cyanophenol (1.2 g), potassium carbonate (1.5 mol equivalents) and the compound being tested as a catalyst (10 mol %). The reaction mixtures were held, with stirring, at 40° C. for 4 hrs, then at 60° C. for 2 hrs. The reaction was monitored for loss of starting material and formation of product, throughout the hold periods, by Gas Chromatography. Results are recorded as area % levels of methyl (E)-2-{2-[6-chloropyrimidin-4-yloxy]phenyl}-3-methoxyacrylate (II) and methyl (E)-2-{2-[6-(2-cyanophenoxy)pyrimidin-4-yloxy]phenyl}-3-methoxyacrylate (I) in the reaction mixture.

The following systems were tested:

TABLE 3

| No. | Solvent | Catalyst | Base |
|---|---|---|---|
| 2.1 | DMF | No Catalyst | $K_2CO_3$ (1.9 g) |
| 2.2 | DMF | DABCO (0.10 g) | $K_2CO_3$ (1.9 g) |
| 2.3 | DMF | 3-Quinuclidinone Hydrochloride (0.15 g) | $K_2CO_3$ (1.9 g) |
| 2.4 | DMF | 3-Quinuclidinol (0.11 g) | $K_2CO_3$ (1.9 g) |
| 2.5 | DMF | 4-Methylmorpholine (0.09 g) | $K_2CO_3$ (1.9 g) |
| 2.6 | DMF | DMAP (0.11 g) | $K_2CO_3$ (1.9 g) |
| 2.7 | DMF | Dimethyloctylamine (0.14 g) | $K_2CO_3$ (1.9 g) |

The results are shown in Table 4 below:

TABLE 4

| No. | 4 hr at 40° C. | | +2 hr at 60° C. | |
|---|---|---|---|---|
| | Residual (II) | (I) Formed | Residual (II) | (I) Formed |
| 2.1 | 90.5% | 7.5% | 64.7% | 31.8% |
| 2.2 | 0.6% | 94.1% | 0.5% | 94.9% |
| 2.3 | 80.1% | 17.1% | 50.3% | 45.8% |
| 2.4 | 0.4% | 94.4% | 0.5% | 94.1% |
| 2.5 | 91.3% | 6.6% | 75.3% | 21.4% |
| 2.6 | 91.4% | 6.7% | 69.2% | 27.4% |
| 2.7 | 83.4% | 14.1% | 55.8% | 40.3% |

Example 2 a) Coupling of Methyl (E)-2-{2-[6-chloropyrimidin-4-yloxy]phenyl}-3-methoxyacrylate with 2-cyanophenol in DMF with 5.0 mol % Quinuclidine Hydrochloride Added After the 2-cyanophenol A stirred solution of (E)-2-{2-[6-chloropyrimidin-4-yloxy]phenyl}-3-methoxyacrylate (80.0 g at 98% w/w, 0.24 mols) in DMF (80 g) was heated to approximately 50° C. and then potassium carbonate (51.6 g at 98% w/w, 0.37 mols) was added. The mixture was heated to 60° C. and a solution of 2-cyanophenol in DMF was added (63.9 g at 50% w/w, 0.27 mols), followed by quinuclidine hydrochloride (1.85 g at 97% w/w, 0.012 mols). The reaction mixture was heated to 80° C. (exotherm took the temperature to 91° C.) and held for 20 minutes when analysis indicated that the reaction was complete. The DMF was distilled off under vacuum to a final temperature of 100° C. and then toluene (134.8 g) was charged, followed by hot water (259.4 g), maintaining the temperature of the mixture above 70° C. The mixture was stirred at 80° C. for 30 minutes, settled and then the aqueous phase separated. The toluene phase (233.0 g) contained methyl (E)-2-{2-[6-(2-cyanophenoxy)pyrimidin-4-yloxy]phenyl}-3-methoxyacrylate (41.4% w/w) 98.1% of theory.

b) Coupling of Methyl (E)-2-{2-[6-chloropyrimidin-4-yloxy]phenyl}-3-methoxyacrylate with 2-cyanophenol in DMF with 5.0 mol % Quinuclidine Hydrochloride Added Before the 2-cyanophenol A stirred solution of (E)-2-{2-[6-chloropyrimidin-4-yloxy]phenyl}-3-methoxyacrylate (80.0 g at 98% w/w, 0.24 mols) in DMF (80 g) was heated to approximately 50° C. and then potassium carbonate (51.6 g at 98% w/w, 0.37 mols) was added. The mixture was heated to 60° C. and quinuclidine hydrochloride (1.85 g at 97% w/w, 0.012 mols) was charged. The mixture was held at 60° C. for 10 minutes before adding a solution of 2-cyanophenol in DMF (63.9 g at 50% w/w, 0.27 mols). The mixture was heated to 80° C. (exotherm took the temperature to 85° C.) and held for 90 minutes when analysis indicated that the reaction was complete. The DMF was distilled off under vacuum to a final temperature of 100° C. and then toluene (134.8 g) was charged, followed by hot water (259.4 g), maintaining the temperature of the mixture above 70° C. The mixture was stirred at 80° C. for 30 minutes, settled and then the aqueous phase separated. The toluene phase (230.6 g) contained methyl (E)-2-{2-[6-(2-cyanophenoxy)pyrimidin-4-yloxy]phenyl}-3-methoxyacrylate (35.8% w/w) 84.0% of theory.

c) Coupling of Methyl (E)-2-{2-[6-chloropyrimidin-4-yloxy]phenyl}-3-methoxyacrylate with 2-cyanophenol in MIBK with 5.0 mol % Quinuclidine Hydrochloride Added After the 2-cyanophenol A stirred solution of (E)-2-{2-[6-chloropyrimidin-4-yloxy]phenyl}-3-methoxyacrylate (80.0 g at 98% w/w, 0.24 mols) in MIBK (80 g) was heated to approximately 50° C. and then potassium carbonate (51.6 g at 98% w/w, 0.37 mols) was added. The mixture was heated to 60° C. and 2-cyanophenol (32.8 g at 97.5% w/w, 0.27 mols), and a further charge of MIBK (32.0 g) was added, followed, after 1 minute, by quinuclidine hydrochloride (1.85 g at 97% w/w, 0.012 mols). The reaction mixture was heated to 80° C. (exotherm took the temperature to 89° C.) and held for 30 minutes when analysis indicated that the reaction was complete. Hot water (259.4 g) was added, maintaining the temperature above 70° C. The mixture was stirred at 80° C. for 30 minutes, settled and then the aqueous phase separated. The MIBK phase (215.0 g) contained methyl (E)-2-{2-[6-(2-cyanophenoxy)pyrimidin-4-yloxy]phenyl}-3-methoxyacrylate (45.8% w/w) 100% of theory.

d) Coupling of Methyl (E)-2-{2-[6-chloropyrimidin-4-yloxy]phenyl}-3-methoxyacrylate with 2-cyanophenol in DMF with 1.0 mol % Quinuclidine Hydrochloride Added After the 2-cyanophenol A stirred solution of (E)-2-{2-[6-chloropyrimidin-4-yloxy]phenyl}-3-methoxyacrylate (80.0 g at 98% w/w, 0.24 mols) in DMF (80 g) was heated to approximately 50° C. and then potassium carbonate (51.6 g at 98% w/w, 0.37 mols) was added. The mixture was heated to 60° C. and a solution of 2-cyanophenol in DMF was added (63.9 g at 50% w/w, 0.27 mols), followed by quinuclidine hydrochloride (0.37 g at 97% w/w, 0.002 mols). The reaction mixture was heated to 80° C. (exotherm took the temperature to 89° C.) and held for 20 minutes when analysis indicated that the reaction was complete. The DMF was distilled off under vacuum to a final temperature of 100° C. and then toluene (134.8 g) was charged, followed by hot water (259.4 g), maintaining the temperature of the mixture above 70° C. The mixture was stirred at 80° C. for 30 minutes, settled and then the aqueous phase separated. The toluene phase (233.0 g) contained methyl (E)-2-{2-[6-(2-cyanophenoxy)pyrimidin-4-yloxy]phenyl}-3-methoxyacrylate (41.3% w/w) 97.9% of theory.

e) Coupling of Methyl (E)-2-{2-[6-chloropyrimidin-4-yloxy]phenyl}-3-methoxyacrylate with 2-cyanophenol in DMF with 0.2 mol % Quinuclidine Hydrochloride Added After the 2-cyanophenol A stirred solution of (E)-2-{2-[6-chloropyrimidin-4-yloxy]phenyl}-3-methoxyacrylate (80.0 g at 98% w/w, 0.24 mols) in DMF (80 g) was heated to approximately 50° C. and then potassium carbonate (51.6 g at 98% w/w, 0.37 mols) was added. The mixture was heated to 60° C. and a solution of 2-cyanophenol (32.8 g at 97.5% w/w, 0.27 mols) in DMF (32 g) was added, followed by quinuclidine hydrochloride (0.07 g at 97% w/w, 0.0005 mols). The reaction mixture was heated to 80° C. (exotherm took the temperature to 85° C.) and held for 105 minutes when analysis indicated that the reaction was complete. The DMF was distilled off under vacuum to a final temperature of 100° C. and then toluene (134.8 g) was charged, followed by hot water (259.4 g), maintaining the temperature of the mixture above 70° C. The mixture was stirred at 80° C. for 30 minutes, settled and then the aqueous phase separated.

The toluene phase (229.8 g) contained methyl (E)-2-{2-[6-(2-cyanophenoxy)pyrimidin-4-yloxy]phenyl}-3-methoxyacrylate (40.5% w/w) 94.7% of theory.

f) Coupling of Methyl (E)2-{2-[6-chloropyrimidin-4-yloxy]phenyl}-3-methoxyacrylate with 2-cyanophenol in DMF with No Catalyst Present A stirred slurry containing methyl (E)-2-{2-[6-chloropyrimidin-4-yloxy]phenyl}-3-methoxyacrylate (80.9 g at 99%, 0.25 mols), potassium carbonate (52.8 g at 98%, 0.375 mols) and 2-cyanophenol (33.6 g at 97.5%, 0.275 mols) in DMF (130 mols) was heated to 80° C. and held at this temperature for 8 hours. The DMF was removed by vacuum distillation to a maximum temperature of 100° C. Toluene (160 ml) was added to the distillation residues, maintaining the temperature between 60-70° C., followed by water (265 mls) which had been heated to 60° C., again maintaining the temperature between 60-70° C. The mixture was stirred for 40 minutes at 80° C. and then settled and the lower aqueous phase separated. The toluene solution (223.3 g) contained methyl (E)-2-{2-[6-(2-cyanophenoxy)pyrimidin-4-yloxy]phenyl}-3-methoxyacrylate (38.8% w/w) 86.6% of theory.

g) Coupling of Methyl (E)-2-{2-[6-chloropyrimidin-4-yloxy]phenyl}-3-methoxyacrylate with 2-cyanophenol in DMF with 5.0 mol % of 3-quinuclidinol Added After the 2-cyanophenol A stirred solution of (E)-2-{2-[6-chloropyrimidin-4-oxy]phenyl}-3-methoxyacrylate (80.0 g at 98% w/w, 0.24 mols) in DMF (80 g) was heated to approximately 60° C. and then potassium carbonate (51.6 g at 98% w/w, 0.37 mols) was added. After 5 minutes 2-cyanophenol (32.8 g at 97.5% w/w, 0.27 mols) was added, followed, after a further 5 minutes, by 3-quinuclidinol (1.60 g at 97% w/w, 0.012 mols). The reaction mixture was heated to 80° C. (exotherm took the temperature to 84° C.) and held for 10 minutes when analysis indicated that the reaction was complete. The DMF was removed by vacuum distillation to a maximum temperature of 100° C. The temperature of the distillation residues was adjusted to 80° C., then toluene (134.8 g) and hot water (259.4 g) were added, maintaining the temperature above 70° C. The mixture was stirred at 80° C. for 30 minutes, settled and then the aqueous phase separated. The toluene phase (225.4 g) contained methyl (E)-2-{2-[6-(2-cyanophenoxy)pyrimidin-4-yloxy]phenyl}-3-methoxyacrylate (40.8% w/w) 93.6% of theory.

h) Coupling of Methyl (E)-2-{2-[6-chloropyrimidin-4-yloxy]phenyl}-3-methoxyacrylate with 2-cyanophenol in DMF with 5.0 mol % 3-quinuclidinone Hydrochloride Added After the 2-cyanophenol A stirred solution of (E)-2-{2-[6-chloropyrimidin-4-yloxy]phenyl}-3-methoxyacrylate (80.0 g at 98% w/w, 0.24 mols) in DMF (80 g) was heated to approximately 60° C. and then potassium carbonate (51.6 g at 98% w/w, 0.37 mols), 2-cyanophenol (32.8 g at 97.5% w/w, 0.27 mols) in DMF (32.8 g) and quinuclidinone hydrochloride (2.03 g at 97% w/w, 0.012 mols were added at five minute intervals. The reaction mixture was heated to 80° C. and held at this temperature for 195 minutes when analysis indicated that the reaction was complete. The DMF was distilled off under vacuum to a final temperature of 100° C. and then toluene (134.8 g) was charged, followed by hot water (259.4 g), maintaining the temperature of the mixture above 70° C. The mixture was stirred at 80° C. for 30 minutes, settled and then the aqueous phase separated. The toluene phase (226.4 g) contained methyl (E)-2-{2-[6-(2-cyanophenoxy)pyrimidin-4-yloxy]phenyl}-3-methoxyacrylate (41.58% w/w) 95.8% of theory.

i) Coupling of Methyl (E)-2-{2-[6-chloropyrimidin-4-yloxy]phenyl}-3-methoxyacrylate with 2-cyanophenol in DMF with 13.0 mol % N-methyl Pyrrolidine Added After the 2-cyanophenol A stirred DMF solution (211.2 g) containing (E)-2-{2-[6-chloropyrimidin-4-yloxy]phenyl}-3-methoxyacrylate (45.5% w/w, 0.3 mols) was adjusted to approximately 50° C. A solution of 2-cyanophenol in DMF (78.5 g at 50% w/w, 0.33 mols) and potassium carbonate (63.5 g at 98% w/w, 0.45 mols) were added and the mixture stirred for one minute before adding N-methyl pyrrolidine (3.5 g at 97% w/w, 0.04 mols). The reaction mixture was heated to 60° C. and held at this temperature for 90 minutes. The mixture was then heated to 85° and the DMF removed by vacuum distillation to an end temperature of 100° C. Toluene (165.8 g) was charged, followed by hot water (318.6 g), maintaining the temperature of the mixture at 80° C. The mixture was stirred at 80° C. for 30 minutes, settled and then the aqueous phase separated. The toluene phase (296.8 g) was vacuum distilled to remove the solvent. The distillation residues were cooled to 80° C. and then methanol (88 g) added, maintaining the temperature above 60° C. The solution was cooled to 5° C. and (E)-2-{2-[6-(2-cyanophenoxy)pyrimidin-4-yloxy]phenyl}-3-methoxyacrylate isolated by filtration (84.7% of theory). The methanol filtrates contained (E)-2-{2-[6-(2-cyanophenoxy)pyrimidin-4-yloxy]phenyl}-3-methoxyacrylate (4.8% of theory)

j) Coupling of Methyl (E)-2-{2-[6-chloropyrimidin-4-yloxy]phenyl}-3-methoxyacrylate with 2-cyanophenol in DMF with 5.0 mol % N-methyl Pyrrolidine Added After the 2-cyanophenol A stirred DMF solution (211.2 g) containing (E)-2-{2-[6-chloropyrimidin-4-yloxy]phenyl}-3-methoxyacrylate (45.5% w/w, 0.3 mols) was adjusted to approximately 40-50° C. A solution of 2-cyanophenol in DMF (78.5 g at 50% w/w, 0.33 mols) and potassium carbonate (63.5 g at 98% w/w, 0.45 mols) were added and the mixture stirred for 5 minute before adding N-methyl pyrrolidine (1.32 g at 97% w/w, 0.015 mols) .The reaction mixture was heated to 80° C. and held at this temperature for 4 hours. The DMF was removed by vacuum distillation to an end temperature of 100° C. Toluene (165.8 g) was charged, followed by hot water (318.6 g), maintaining the temperature of the mixture at 80° C. The mixture was stirred at 80° C. for 30 minutes, settled and then the aqueous phase separated. The toluene phase (298.5 g) was vacuum distilled to remove the solvent. The distillation residues were cooled to 80° C. and then methanol (88 g) added, maintaining the temperature above 60° C. The solution was cooled to 5° C. and (E)-2-{2-[6-(2-cyanophenoxy)pyrimidin-4-yloxy]phenyl}-3-methoxyacrylate isolated by filtration (81.4% of theory). The methanol filtrates contained (E)-2-{2-[6-(2-cyanophenoxy)pyrimidin-4-yloxy]phenyl}-3-methoxyacrylate (6.8% of theory).

k) Coupling of Crude Methyl (E)-2-{2-[6-chloropyrimidin-4-yloxy]phenyl}-3-methoxyacrylate with 2-cyanophenol in DMF with 5.0 mol % Quinuclidine Hydrochloride Added After the 2-cyanophenol A stirred DMF solution of (E)-2-{2-[6-chloropyrimidin-4-yloxy]phenyl}-3-methoxyacrylate (193.0 g at 47.12% w/w, 0.283 mols) was heated to approximately 60° C. and then potassium carbonate (59.8 g at 98% w/w, 0.42 mols) was added, followed by a solution of 2-cyanophenol (38.0 g at 97.5% w/w, 0.31 mols) in DMF (39.4 g). Finally, quinuclidine hydrochloride (2.16 g at 97% w/w, 0.014 mols) was added and the reaction mixture was heated to 80° C. and held at this temperature for 10 minutes when analysis indicated that the reaction was complete. The DMF was distilled off under vacuum to a final temperature of 100° C. and then toluene (156.4 g) was charged, followed by hot water (300.9 g), maintaining the temperature of the mixture above 70° C. The mixture was stirred at 80° C. for 30 minutes, settled and then the aqueous phase separated. The toluene phase (281.2 g) contained methyl (E)-2-{2-[6-(2-cyanophenoxy)pyrimidin-4-yloxy]phenyl}-3-methoxyacrylate (38.4% w/w) 94.7% of theory.

l) Coupling of Methyl 2-[2-(6-chloropyrimidin-4-yloxy)phenyl]-3,3-dimethoxypropanoate with 2-cyanophenol in Isopropyl Acetate with 6.7 mol % of Quinuclidine Hydrochloride Added After 2-cyanophenol To a stirred vessel containing isopropyl acetate (160.3 g) at room temperature, was added, 2-cyanophenol (14.95 g at 99% w/w, 0.12 mols), potassium carbonate (18.31 g at 98% w/w, 0.13 mols) and methyl 2-[2-(6-chloropyrimidin-4-yloxy)phenyl]-3,3-dimethoxypropanoate (40.0 g at 99.2% w/w, 0.113 mols) which contained methyl (E)-2-{2-[6-chloropyrimidin-4-yloxy]phenyl}-3-methoxyacrylate (0.104 g, $3.2 \times 10^{-4}$ mols). The mixture was heated to 60° C. and held at this temperature for 10 minutes. Quinuclidine hydrochloride (1.14 g at 97% w/w, 0.0075 mols) was added and the reaction mixture heated to reflux (approximately 90° C.) for 3 hours (the reaction was complete in 1.75 hours). The reaction mixture was cooled to 85° C. and then water (100 g) was added maintaining the temperature above 70° C. After stirring at 75° C. for 15 minutes the mixture was settled and the aqueous phase separated. A second water wash (100 g) was applied in the same way. The remaining isopropyl acetate solution (249.5 g) contained methyl 2-[2-[6-(2-cyanophenoxy)-pyrimidin-4-yloxy]phenyl]-3,3-dimethoxy propanoate (19.11% w/w), 96.2% of theory, and methyl (E)-2-{2-[6-(2-cyanophenoxy)pyrimidin-4-yloxy]phenyl}-3-methoxyacrylate (0.41% w/w), 2.2% of theory.

m) Coupling of Methyl 2-[2-(6-chloropyrimidin-4-yloxy)phenyl]-3,3-dimethoxypropanoate with 2-cyanophenol in Isopropyl Acetate with 1.4 mol % of Quinuclidine Hydrochloride Added After 2-cyanophenol To a stirred vessel containing isopropyl acetate (160.3 g) at room temperature, was added, 2-cyanophenol (14.95 g at 99% w/w, 0.12 mols), potassium carbonate (18.31 g at 98% w/w, 0.13 mols) and methyl 2-[2-(6-chloropyrimidin-4- yloxy)phenyl]-3,3-dimethoxypropanoate (40.0 g at 99.2% w/w, 0.113 mols) which contained methyl (E)-2-{2-[6-chloropyrimidin-4-yloxy]phenyl}-3-methoxyacrylate (0.104 g, $3.2 \times 10^{-4}$ mols). The mixture was heated to 60° C. and held at this temperature for 10 minutes. Quinuclidine hydrochloride (0.24 g at 97% w/w, 0.0016 mols) was added and the reaction mixture heated to reflux (approximately 90° C.) for 4.5 hours (the reaction was complete in 4 hours). The reaction mixture was cooled to 80-85° C. and then water (100 g) was added maintaining the temperature above 75° C. After stirring at 75-80° C. for 15 minutes the mixture was settled and the aqueous phase separated. A second water wash (100 g) was applied in the same way. The remaining isopropyl acetate solution (205.8 g) contained methyl 2-[2-[6-(2-cyanophenoxy)-pyrimidin-4-yloxy]phenyl]-3,3-dimethoxy propanoate (22.3% w/w), 93.3% of theory, and methyl (E)-2-{2-[6-(2-cyanophenoxy)pyrimidin-4-yloxy]phenyl}-3-methoxyacrylate (0.52% w/w), 2.3% of theory.

n) Coupling of Methyl 2-[2-(6-chloropyrimidin-4-yloxy)phenyl]-3,3-dimethoxypropanoate with 2-cyanophenol in Isopropyl Acetate with 1.4 mol % of Quinuclidine Hydrochloride Added efore 2-cyanophenol To a stirred vessel containing isopropyl acetate (160.3 g) at room temperature, was added, potassium carbonate (18.31 g at 98% w/w, 0.13 mols) and methyl 2-[2-(6-chloropyrimidin-4-yloxy)phenyl]-3,3-dimethoxypropanoate (40 g at 99.2% w/w, 0.113 mols) which contained methyl (E)-2-{2-[6-chloropyrimidin-4-yloxy]phenyl}-3-methoxyacrylate (0.1 g, $3 \times 10^{-4}$ mols) and quinuclidine hydrochloride (0.24 g at 97% w/w, 0.0016 mols). The mixture was heated to 60° C. and held at this temperature for 10 minutes. 2-cyanophenol (14.95 g at 99% w/w, 0.12 mols) was added and the reaction mixture heated to reflux (approximately 90° C.) for 5 hours. The reaction mixture was brought to 85° C. and then water (100 g) was added maintaining the temperature above 75° C. After stirring at 75-80° C. for 15 minutes the mixture was settled and the aqueous phase separated. A second water wash (100 g) was applied in the same way. The remaining isopropyl acetate solution (210.0 g) contained methyl 2-[2-[6-(2-cyanophenoxy)-pyrimidin-4-yloxy]phenyl]-3,3-dimethoxy propanoate (21.97% w/w), 93.8% of theory, and methyl (E)-2-{2-[6-(2-cyanophenoxy)pyrimidin-4-yloxy]phenyl}-3-methoxyacrylate (0.65% w/w), 3.0% of theory.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A process for preparing a compound of formula (I)

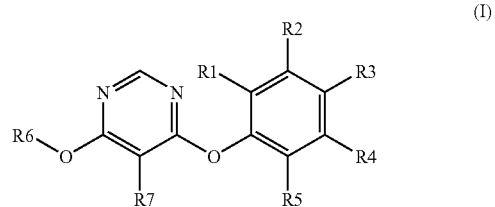

which comprises:

reacting a compound of formula (II)

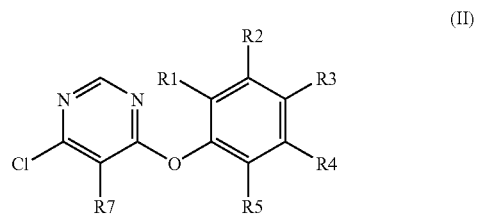

with a compound of formula R6-OH, or a salt thereof, in the presence of between 0.05 and 40 mol % of quinuclidine, 3-quinuclidinol or 3-quinuclidinone or an acid salt of quinuclidine, 3-quinuclidinol or 3-quinuclidinone, wherein:

R1, R2, R3 and R4 are, independently, hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, alkoxy, alkylthio, alkylsulphinyl or alkylsulphonyl;

R5 is hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, alkoxy, alkylthio, alkylsulphinyl or alkylsulphonyl, or

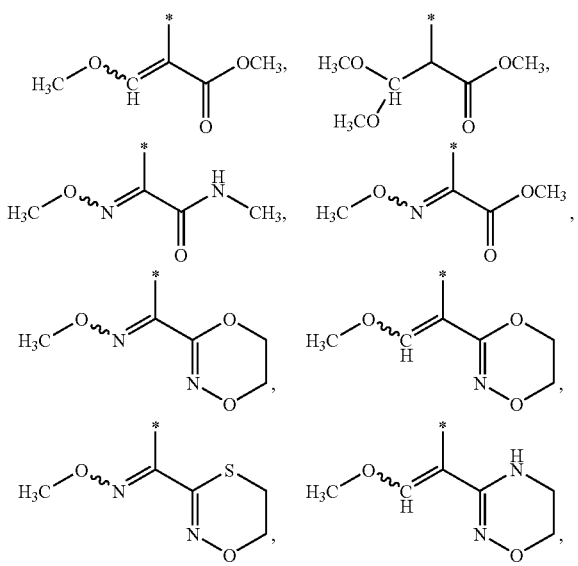

-continued

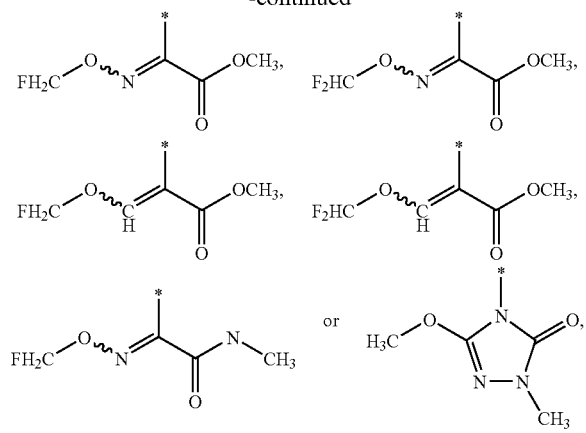

wherein * denotes the point of attachment to the phenyl radical of formula (I);

R6 is substituted or unsubstituted aryl or heterocyclyl, or the salt thereof;

R7 is hydrogen, fluorine, chlorine or bromine, with the proviso that R6 and the radical:

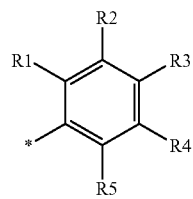

are different from each other.

2. The process of claim 1, wherein the catalyst is quinuclidine or 3-quinuclidinol or an acid salt of quinuclidine or 3-quinuclidinol.

3. The process of claim 1, wherein the acid salt is the hydrochloride salt.

4. The process of claim 1, wherein the catalyst is bound to a polymeric support through one of positions 3, 4, 5 or 8 of the quinuclidine ring.

5. The process of claim 1, wherein R1, R2, R3 and R4 are, independently, hydrogen, fluorine, chlorine, bromine, cyano, nitro, acetyl, propionyl, methoxycarbonyl, ethoxycarbonyl, aminocarbonyl, methylaminocarbonyl, ethylaminocarbonyl, dimethylaminocarbonyl, diethylaminocarbonyl, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

6. The process of claim 5, wherein R1, R2, R3 and R4 are, independently, hydrogen or methyl.

7. The process of claim 6, wherein R1, R2, R3 and R4 are each hydrogen.

8. The process of claim 1, wherein R5 is:

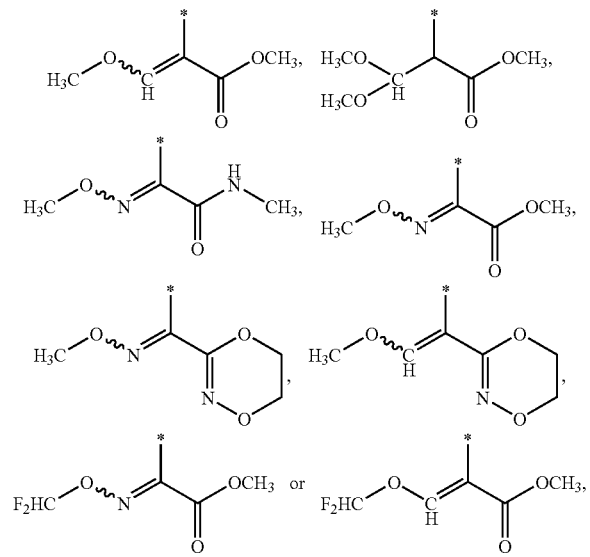

or a mixture thereof, where * denotes the point of attachment to the phenyl radical.

9. The process of claim 8, wherein R5 is:

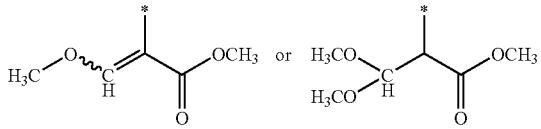

or a mixture thereof, where * denotes the point of attachment to the phenyl radical.

10. The process of claim 1, wherein R6 is:
(a) a heterocycle having 3 to 7 ring members, optionally substituted by halogen or by $C_{1-6}$ alkyl, $C_{1-6}$ alkoxy, $C_{1-6}$ halogenoalkyl or $C_{1-6}$ halogenoalkoxy; or
(b) phenyl or naphthyl, each of which is optionally mono- to pentasubstituted by identical or different substituents selected from the group comprising:
  (i) halogen, cyano, formyl or acetal protected formyl, carboxyl, carbamoyl, thiocarbamoyl, aminocarbonyl;
  (ii) $C_{1-8}$, straight-chain or branched, alkyl, oxyalkyl, alkoxy, alkoxyalkyl, alkylthioalkyl, dialkoxyalkyl, alkylthio, alkylsuphinyl or alkylsulphonyl having in each case 1 to 8 carbon atoms;
  (iii) $C_{2-6}$, straight-chain or branched, alkenyl or alkenyloxy;
  (iv) $C_{1-6}$, straight-chain or branched, halogenoalkyl, halogenoalkoxy, halogenoalkylthio, halogenoalkylsulphinyl or halogenoalkylsulphonyl with between 1 and 13 identical or different halogen atoms;
  (v) $C_{2-6}$, straight chain or branched, halogenoalkenyl or halogenoalkenyloxy with between 1 and 11 identical or different halogen atoms;
  (vi) $C_{1-6}$, straight-chain or branched, dialkylamino; alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl;
  (vii) $C_{3-6}$ cycloalkyl or cycloalkyloxy;

(viii) doubly attached $C_{3-4}$ alkylene, $C_{2-3}$ oxyalkylene or $C_{1-2}$ dioxyalkylene, each of which is optionally mono- to tetrasubstituted by identical or different substituents selected from the group consisting of fluorine, chlorine, oxo, methyl, trifluoromethyl and ethyl; or (ix) the group

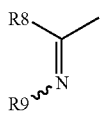

in which:
R8 is hydrogen, hydroxyl, $C_{1-4}$ alkyl or $C_{1-6}$ cycloalkyl; and
R9 is
  ii. hydroxyl, methoxy, ethoxy, amino, methylamino, phenyl or benzyl; or
  iii. $C_{1-4}$ alkyl or alkoxy, optionally substituted with cyano-, alkylthio-, alkylamino-, dialkylamino- or phenyl;
  iv. $C_{2-4}$ alkenyloxy or alkynyloxy;
  v. benzoyl, benzoylethenyl, cinnamoyl, heterocyclyl; or
  vi. phenylalkyl, phenylalkyloxy or heterocyclylalkyl, having in each case 1 to 3 carbon atoms in the alkyl moieties and being in each case optionally mono- to trisubstituted in the ring moiety by halogen and/or straight-chain or branched $C_{1-4}$ alkyl or alkoxy.

11. The process of claim 10, wherein R6 is optionally mono- to pentasubstituted phenyl where the substituents are selected from halogen, cyano, formyl or acetal protected formyl, methoxycarbonyl, ethoxycarbonyl, aminocarbonyl, methylaminocarbonyl, ethylaminocarbonyl, dimethylaminocarbonyl, diethylaminocarbonyl, in each case straight-chain or branched $C_{1-4}$ alkyl or halogenoalkyl or the group:

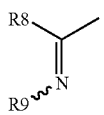

wherein R8 is hydrogen and R9 is hydroxyl, methoxy or ethoxy.

12. The process of claim 11, wherein R6 is cyanophenyl.
13. The process of claim 12, wherein R6-OH is 2-cyanophenol.
14. The process of claim 1, wherein R7 is hydrogen, fluorine or chlorine.
15. The process of claim 14, wherein R7 is hydrogen.
16. The process of claim 1, wherein R1, R2, R3 and R4 are hydrogen, R5 is

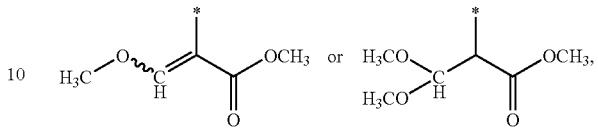

or a mixture thereof, R6 is 2-cyanophenyl and R7 is hydrogen.

17. The process of claim 1, which is carried out in the presence of between 0.1 and 20 mol % of catalyst.
18. The process of claim 17, which is carried out in the presence of between 0.1 and 5 mol % of catalyst.
19. The process of claim 18, which is carried out in the presence of between 0.2 and 5 mol % of catalyst.
20. The process of claim 1, which is carried out in an inert solvent or diluent.
21. The process of claim 20 in which the inert solvent or diluent is methyl isobutyl ketone, cyclohexanone, N,N-diisopropylethylamine, isopropyl acetate or N,N-dimethylformamide.
22. The process of claim 21 in which the inert solvent or diluent is isopropyl acetate or N,N-dimethylformamide.
23. The process of claim 22 in which the inert solvent or diluent is N,N-dimethylformamide.
24. The process of claim 1, which is carried out in an aqueous organic solvent system using a salt of R6-OH or the compound of formula (IV).
25. The process of claim 24, wherein the organic solvent is cyclohexanone, methyl isobutyl ketone, isopropyl acetate, or N,N-dimethylformamide.
26. The process of claim 24, wherein the salt is a lithium, cesium, sodium, potassium, 1,5-diazabicyclo[4.3.0]non-5-ene or 1,8-diazabicyclo[5.4.0]undec-7-ene salt.
27. The process of claim 26, wherein the salt is a sodium or potassium salt.
28. The process of claim 27, wherein salt is a potassium salt.
29. The process of claim 1, which is carried out in the presence of an acid acceptor.
30. The process of claim 29, wherein the acid acceptor is potassium carbonate or sodium carbonate.
31. The process of claim 1, which is carried out at a temperature of from 0 to 120° C.

* * * * *